United States Patent
Majeed et al.

(10) Patent No.: US 11,332,702 B2
(45) Date of Patent: May 17, 2022

(54) **ALCOHOLIC BEVERAGE COMPOSITION CONTAINING *BACILLUS COAGULANS***

(71) Applicants: Muhammed Majeed, Edison, NJ (US); Kalyanam Nagabhushanam, East Windsor, NJ (US); Sivakumar Arumugam, Bangalore (IN); Furqan Ali, Bangalore (IN); Shaheen Majeed, Springville, UT (US); Kirankumar Beede, Bangalore (IN)

(72) Inventors: Muhammed Majeed, Edison, NJ (US); Kalyanam Nagabhushanam, East Windsor, NJ (US); Sivakumar Arumugam, Bangalore (IN); Furqan Ali, Bangalore (IN); Shaheen Majeed, Springville, UT (US); Kirankumar Beede, Bangalore (IN)

(73) Assignee: SAMI LABS LIMITED, Bangalore (IN)

( * ) Notice: Subject to any disclaimer, the term of this patent is extended or adjusted under 35 U.S.C. 154(b) by 14 days.

(21) Appl. No.: 16/136,475

(22) Filed: Sep. 20, 2018

(65) Prior Publication Data

US 2019/0085277 A1 Mar. 21, 2019

(30) Foreign Application Priority Data

Sep. 21, 2017 (IN) .............................. 201741033477

(51) Int. Cl.
| | |
|---|---|
| *C12C 12/00* | (2006.01) |
| *A61K 35/742* | (2015.01) |
| *A23L 33/135* | (2016.01) |
| *A61K 9/00* | (2006.01) |
| *A61K 35/00* | (2006.01) |

(52) U.S. Cl.
CPC .......... *C12C 12/008* (2013.01); *A23L 33/135* (2016.08); *A61K 9/0095* (2013.01); *A61K 35/742* (2013.01); *A23V 2002/00* (2013.01); *A61K 2035/115* (2013.01)

(58) Field of Classification Search
None
See application file for complete search history.

(56) References Cited

U.S. PATENT DOCUMENTS

| | | | | |
|---|---|---|---|---|
| 4,251,632 A * | 2/1981 | Chen | ........................ | C12P 19/24 435/180 |
| 8,568,743 B2 * | 10/2013 | Farmer | .................... | A61P 31/20 424/282.1 |
| 9,579,352 B2 * | 2/2017 | Majeed | ................ | A61K 35/742 |
| 10,287,641 B2 * | 5/2019 | Olofsson | ................ | C12G 3/025 |
| 10,306,908 B2 * | 6/2019 | Segawa | ..................... | A23L 2/40 |

FOREIGN PATENT DOCUMENTS

WO 2018182512 A1 10/2018

OTHER PUBLICATIONS

Rizk et al. "The Use of Ethanol for the Selective Isolation of Bacillus Strains Originating from Spores". Zentralbl. Mikrobiol. 144 (1989), 123-128.*
Guidelines for the evaluation of probiotics in food, Joint FAO/WHO Working Group Report on Drafting Guidelines for the Evaluation of Probiotics in Food, London, Ontario, Canada, Apr. 30 and May 1, 2002, section 3.1.
Indian Council of Medical Research/Department of Biotechnology, Ministry of Science and Technology, Government of India, New Delhi), ICMR-DBT Guidelines for Evaluation of Probiotics in Food, 2011), Section 2, Subsection 2.3).
Singh et al., (2013) Role of probiotics in health and disease: a review, JPMA, The Journal of the Pakistan Medical Association, 63(2):253-25).
Bode et al.,(2003) Effect of alcohol consumption on the gut, Best Practice & Research Clinical Gastroenterology; 17(4):575-592).
Bob Roehr et al. 2016, Drinking Causes Gut Microbe Imbalance Linked to Liver Disease, The Scientific American, https://www.scientificamerican.com/article/drinking-causes-gut-microbe-imbalance-linked-to-liver-disease/.
Kirpich et al. (2008) Probiotics restore bowel flora and improve liver enzymes in human alcohol-induced liver injury: a pilot study; Alcohol; 42(8):675-682).
Mannu et al. (2003) International Journal of Food Microbiology 88 (2003) 291-304.
Guidelines for the evaluation of probiotics in food, Joint FAO/WHO Working Group Report on Drafting Guidelines for the Evaluation of Probiotics in Food, London, Ontario, Canada, Apr. 30 and May 1, 2002.
Indian Council of Medical Research/Department of Biotechnology, Ministry of Science and Technology, Government of India, New Delhi), ICMR-DBT Guidelines for Evaluation of Probiotics in Food, 2011).
ProDURA® Bacillus coagulans Demonstrates Superior Heat Resistance, Dr. Jayne Stratton, Research Professor at the University of Nebraska's Food Processing Center, Feb. 2013. https://earthnutri.com/pages/produra%C2%AE.
Philippe Marteau, Evidence of Probiotic Strain Specificity Makes Extrapolation of Results Impossible From a Strain to Another, Even From the Same Species, Annals of Gastroenterology & Hepatology, 2011.

* cited by examiner

Primary Examiner — Vera Afremova

(57) ABSTRACT

A probiotic-alcoholic beverage composition comprising *Bacillus coagulans* is disclosed herein wherein the said spore or vegetative cell of *Bacillus coagulans* exhibited high recovery, tolerability, compatibility and viability of spores and vegetative cells after brewing. Methods for brewing an alcoholic beverage composition comprising *Bacillus coagulans* wherein said spore or bacterium is added during pre-fermentation, during fermentation and post fermentation stages are also disclosed.

4 Claims, 15 Drawing Sheets

ALCOHOLIC BEVERAGE COMPOSITION CONTAINING *BACILLUS COAGULANS*

CROSS-REFERENCE TO RELATED APPLICATIONS

The present application is a PCT filing claiming priority from Indian provisional patent application number IN201741033477 filed on Sep. 21, 2017.

FIELD OF INVENTION

The invention in general relates to probiotics. More specifically the invention relates to alcoholic beverage compositions comprising probiotic bacterium *Bacillus coagulans* and the method of brewing said alcoholic beverage.

DESCRIPTION OF PRIOR ART

Probiotics offer a wide range of health benefits. They are administered as a dietary supplement for the effective management of various diseases like gastrointestinal infections, inflammatory bowel disease, acute and chronic diarrhoea, constipation, abnormal intestinal fermentation, dysbiosis, functional abdominal pain, lactose intolerance, allergies, urogenital infections, cystic fibrosis, metabolic disorders, various cancers, reduction of antibiotic side effects, in oral health such as prevention of dental caries, periodontal diseases and oral malodour, maintenance of a good intestinal environment and balancing the intestinal flora by reducing harmful bacteria (Goldin BR (1998) Health benefits of probiotics, The British Journal of Nutrition 80(4):S203-7; Singh et al., (2013) Role of probiotics in health and disease: a review, JPMA. The Journal of the Pakistan Medical Association, 63(2):253-25).

Consuming alcohol on the pretext of socializing, relaxing and enjoying is on the rise, even with the knowledge that consuming excess alcohol has side effects on the health. Alcohol affects the gut by disturbing intestinal absorption of nutrients including several important vitamins. Studies also report that alcohol significantly modulates the mucosal immune system of the gut (Bode et al., (2003) Effect of alcohol consumption on the gut, Best Practice & Research Clinical Gastroenterology; 17(4):575-592). Alcohol consumption also modifies the gut microflora thereby neutralizing the beneficial effects, the gut microbes provide to the overall health (Bob Roehr, 2016, Drinking Causes Gut Microbe Imbalance Linked to Liver Disease, The Scientific American, scientificamerican.com/article/drinking-causes-gut-microbe-imbalance-linked-to-liver-disease/, accessed 10 Sep. 2018).

There have been many efforts on reversing the effect of alcohol on the gut microflora. Probiotic supplementation has been found to be effective in restoring bowel flora and improving live enzymes in alcohol induced liver damage and hepatotoxicity (Kirpich et al. (2008) Probiotics restore bowel flora and improve liver enzymes in human alcohol-induced liver injury: a pilot study, Alcohol; 42(8):675-682). A Beer, with probiotics present within was also developed to ward off the harmful effects on beer consumption in the gut flora (SG 10201702468S, PROBIOTIC SOUR BEER). However, developing a alcoholic drink with live probiotics is a difficult task since the presence of acidic conditions hinder the growth and survival of the probiotics. The property of the probiotic, in sustaining the harmful conditions also plays a major role in developing an alcoholic beverage containing probiotics. There still exists an unmet industrial need to find a suitable probiotic strain for the development of an alcoholic beverage containing probiotics. The present invention solves the above problem by disclosing an alcoholic beverage composition containing *Bacillus coagulans*, with increased recovery, tolerability, compatibility and viability of spores and vegetative cells of probiotic bacteria *Bacillus coagulans* and the method of brewing the same.

It is the principle objective of the invention to disclose an alcoholic beverage composition containing probiotic bacteria *Bacillus coagulans*.

It is another objective of the invention to disclose a method of brewing an alcoholic beverage composition containing probiotic bacteria *Bacillus coagulans*.

The present invention solves the above objective and provides further related advantages.

SUMMARY OF THE INVENTION

The present invention discloses an alcoholic beverage composition comprising *Bacillus coagulans* in the form of spores or bacterium wherein said spore or bacterium exhibit high recovery, tolerability, compatibility and viability of spores and vegetative cells after brewing. The invention also discloses a method of brewing an alcoholic beverage composition comprising *Bacillus coagulans* wherein said spore or bacterium is added prior to fermentation, during fermentation and post fermentation.

Other features and advantages of the present invention will become apparent from the following more detailed description, taken in conjunction with the accompanying images, which illustrate, by way of example, the principle of the invention.

BRIEF DESCRIPTION OF DRAWINGS

FIG. 5a is the graphical representation showing the stability of probiotic bacteria *Bacillus coagulans* in alcoholic beverage at 40° C., added during the step of packing and pasteurization followed by carbonation while brewing the beverage.

DESCRIPTION OF PREFERRED EMBODIMENTS

Figure 1A:
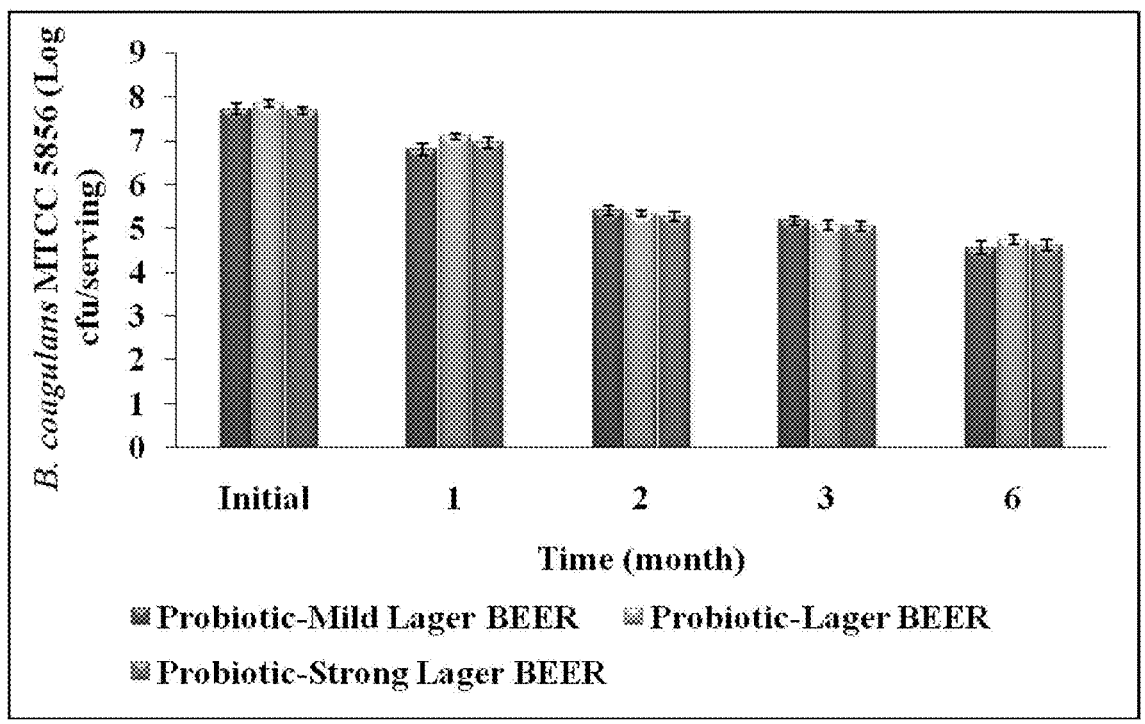
FIG. 1*a* is the graphical representation showing the stability of probiotic bacteria *Bacillus coagulans* in alcoholic beverage, added during the step of malting while brewing the beverage.

In a most preferred embodiment, the invention discloses an alcoholic beverage composition comprising *Bacillus coagulans* in the form of spores or bacterium wherein said spore or bacterium exhibit high recovery, tolerability, compatibility and viability of spores and vegetative cells after brewing. In a related embodiment, the alcoholic beverage is fermented and distilled. In another related embodiment, the alcoholic beverage is carbonated and non-carbonated.

In yet another related embodiment, the fermented alcoholic beverage is selected from the group consisting of, but not limited to, Beer, Ale, Barleywine, Bitter ale, Brown ale, Cask ale, Mild ale, Old ale, Pale ale, Scotch ale, Porter, Stout, Stock ale, Fruit beer, Beer, Lager, Pale lager, Bock, Maerzen/Oktoberfest Beer, Pilsener, Schwarzbier, Sahti, Small beer, Wheat beer, Witbier, Cauim, Chicha, Cider, Perry, Plum jerkum, Desi daru, Huangjiu, Icariine Liquor, Kasiri, Kilju, Kumis, Mead, Nihamanchi, Palm wine, Parakari, Pulque, Sakurá, Sake, Sonti, Tepache, Tiswin, Tonto, Wine, Fortified wine, Port, Madeira, Marsala, Sherry, Vermouth Vinsanto, Fruit wine, Table wine, Sangria, Sparkling wine, Champagne.

In another related embodiment, the distilled alcoholic beverage is selected from the group consisting of, but not limited to, Spirits, Absinthe, Akvavit, Applejack, Arak, Arrack, Awamori, Baijiu, Boroviçka, Brandy, Armagnac, Cognac. Fruit brandy, Eau-de-vie (French), Schnapps—Obstwasser (German), Damassine, Himbeergeist, Kirsch, Poire Williams, Williamine, Cachaça, Gin, Damson gin, Sloe gin, Horilka, Kaoliang, Maotai, Metaxa, Mezcal, Neutral grain spirit, Ogogoro, Ouzo, Palinka, Pisco, Poitin, Rakt, Rakia, Slivovitz, Rum, Shochu, Singani, Soju, Tequila, Tuică, Vodka, Whisky, Bourbon whiskey, Canadian whisky, Irish whiskey, Japanese whisky, ManX Spirit, Rye whiskey, Scotch whisky, Tennessee whiskey, Liqueurs The another embodiment the alcohol content of the beverage composition is between 1% to 43%.

In an embodiment the *Bacillus coagulans* strain is preferably *Bacillus coagulans* MTCC 5856, and strains derived from *Bacillus coagulans* ATCC 31248 and *Bacillus coagulans* ATCC 7050. In another related aspect, the *Bacillus coagulans* live spores/vegetative cells are present in the alcoholic beverages at a concentration of $1 \times 10^6$ to $1 \times 10^{12}$ cfu.

In another preferred embodiment, the composition containing alcoholic beverage and *Bacillus coagulans* is used for therapeutic management of diseases selected from the group consisting of, but not limited to, like gastrointestinal infections, inflammatory bowel disease, acute and chronic diarrhoea, constipation, abnormal intestinal fermentation, dysbiosis, functional abdominal pain, lactose intolerance, allergies, urogenital infections, cystic fibrosis, metabolic disorders, various cancers, reduction of antibiotic side effects, in oral health such as prevention of dental caries, periodontal diseases and oral malodour, maintenance of a good intestinal environment and balancing the intestinal flora by reducing harmful bacteria.

In another preferred embodiment, the invention discloses a method of brewing alcoholic beverage with *Bacillus coagulans*, said method comprising steps of
a) Malting
b) Mashing
c) Filtration
d) Kettle boiling
e) Hops addition
f) Cooling
g) Fermentation with yeast
h) Ageing and clarification
i) Secondary fermentation
j) Carbonation/No carbonation
k) Pasteurization and Packing In a related aspect, the *Bacillus coagulans* spores/vegetative cells are added during pre-fermentation, fermentation and post fermentation stages. In another related aspect, the Bacillus coagulans spores/vegetative cells are added during pre-fermentation stage at step a). In another related aspect, the *Bacillus coagulans* spores/vegetative cells are added during pre-fermentation stage at step e). In another related aspect, the *Bacillus coagulans* spores/vegetative cells are added during fermentation stage at step g). In another related aspect, the *Bacillus coagulans* spores/vegetative cells are added during secondary fermentation stage at step i). In another related aspect, the *Bacillus coagulans* spores/vegetative cells are added during post fermentation stage at step j). In another related aspect, the *Bacillus coagulans* spores/vegetative cells are added during post fermentation stage at step k).

In yet another related aspect, the alcoholic beverage is pasteurized at 60° C. after step i), followed by carbonation/no carbonation step after the addition of *Bacillus coagulans* spores.

In another related aspect, the *Bacillus coagulans* spores/vegetative cells exhibited increased viability and stability throughout the fermentation process.

The specific examples included herein below illustrate the aforesaid most preferred embodiments of the present invention Example 1: Alcoholic Beverage Composition Containing Probiotic Bacteria *Bacillus coagulans*

Methods: Beer samples were procured from local market manufactured by Kingfisher and whisky from McDowell's No. 1. The alcohol content in the Mild lager, Lager, and strong Beer was 3.345%, 3.48% and 4.81% respectively. In whisky the alcohol content was 42.8%. *Bacillus coagulans* MTCC 5856 (Commercially sold as LactoSpore®—from Sabinsa Corporation, NJ, USA) was added to the Beer (Mild lager, Lager, and strong Beer) and Whisky. Beer samples were carbonated and packed in 120 ml container and subjected for stability studies as per the guidelines of International Council for Harmonisation (ICH guidelines Q1A (R2) (ICH 2003). Description of the samples was done based on Visual and organoleptic methods. Specific gravity and pH was determined as per the United State Pharmacopoeia chapter USP<841> and <791> respectively. Other Aerobic micro-organism count was tested as per modified USP <61> method. Yeasts and molds count, *Escherichia coli, Staphylococcus aureus, Pseudomonas aeruginosa*, and *Salmonella* spp. were tested as per USP method chapter <61> and <62>. Enterobacteriaceae test as per USP chapter <2021> and Coliforms as per BAM, Chapter 4 was performed.

Table 1 and Table 2 discloses the Recovery and Tolerability of *Bacillus coagulans* MTCC 5856 spores in alcoholic beverages determined by standard pour plate method.

TABLE 1

Recovery and Tolerability of *Bacillus coagulans* MTCC 5856 spores in alcoholic beverages determined by standard pour plate method.

| Time | Beer (strong lager) with *B. coagulans* MTCC 5856 | | Beer (Mild lager) with *B. coagulans* MTCC 5856 | | Beer (lager) with *B. coagulans* MTCC 5856 | | Whisky with *B. coagulans* MTCC 5856 | |
|---|---|---|---|---|---|---|---|---|
| | $Log_{10}$ CFU/serving | Viability (%) | $Log_{10}$ CFU/serving | Viability (%) | $Log_{10}$ CFU/serving | Viability (%) | $Log_{10}$ CFU/serving | Viability (%) |
| Expected Recovery | 9.544 | 100 | 9.544 | 100 | 9.544 | 100 | 9.544 | 100 |
| | | | | Non-carbonated | | | | |
| After 24 h | 8.992 | 94.22 | 8.968 | 93.97 | 8.851 | 92.75 | 9.041 | 94.73 |
| | | | | Carbonated | | | | |
| After 24 h | 8.877 | 93.01 | 8.895 | 93.21 | 8.884 | 93.09 | ND | ND |

Serving size for Beer is 650 ml and for Whisky it is 100 ml.
ND, Not Done

TABLE 2

Recovery and Tolerability of *Bacillus coagulans* MTCC 5856 spores in alcoholic beverages determined by Flow Cytometry method

| Time | Beer (strong lager) with *B. coagulans* MTCC 5856 | | Beer (Mild lager) with *B. coagulans* MTCC 5856 | | Beer (lager) with *B. coagulans* MTCC 5856 | | Whisky with *B. coagulans* MTCC 5856 | |
|---|---|---|---|---|---|---|---|---|
| | $Log_{10}$ CFU/serving | Viability (%) | $Log_{10}$ CFU/serving | Viability (%) | $Log_{10}$ CFU/serving | Viability (%) | $Log_{10}$ CFU/serving | Viability (%) |
| Expected Recovery | 9.544 | 100 | 9.544 | 100 | 9.544 | 100 | 9.544 | 100 |
| | | | | Non-carbonated | | | | |
| After 24 h | 9.389 | 98.37 | 8.845 | 92.67 | 8.792 | 92.12 | 8.698 | 91.13 |
| | | | | Carbonated | | | | |
| After 24 h | 8.845 | 92.67 | 8.812 | 92.33 | 9.133 | 95.69 | ND | ND |

Serving size for Beer is 650 ml and for Whisky it is 100 ml.
ND, Not Done

Stability Studies at Room temperature (25±2° C., 60%±5% Relative humidity) and accelerated conditions (40±20 C, 65%±5% Relative humidity) were also performed in to determine the stability of the probiotic composition in different alcoholic beverages. The tables 3-10 describe the stability studies of the alcoholic beverage containing probiotic bacteria *Bacillus coagulans* MTCC 5856.

TABLE 3

Probiotic-Mild Lager BEER stability studies at 40 ± 2° C., 65% ± 5% Relative humidity.

| S. No. | Tests performed | Initial | 1 | 2 | 3 | 6 | Limit |
|---|---|---|---|---|---|---|---|
| | | Period of Testing (month) | | | | | |
| 1. | Description | Complies | Complies | Complies | Complies | Complies | Pale brown liquid |
| 2. | Specific gravity | 1.0082 | 1.0083 | 1.0084 | 1.0081 | 1.0085 | Record |
| 3. | pH | 3.86 | 3.84 | 3.81 | 3.82 | 3.79 | Record |
| 4. | Alcohol content by GC | 3.34% | 3.31% | 3.39% | 3.37% | 3.38% | Record |
| 5. | Other Aerobic micro-organism count | <100 cfu/ml | <100 cfu/ml | <100 cfu/ml | <100 cfu/ml | <100 cfu/ml | Record |
| 6. | Yeasts and molds count | Complies | Complies | Complies | Complies | Complies | NMT100 cfu/g |
| 7. | Enterobacteriaceae | Complies | Complies | Complies | Complies | Complies | NMT100 cfu/g |
| 8. | Coliforms | Complies | Complies | Complies | Complies | Complies | NMT10 cfu/g |
| 9. | Pathogens (*Escherichia coli*, *Staphylococcus aureus*, *Pseudomonas aeruginosa*, *Salmonella* spp.) | Complies | Complies | Complies | Complies | Complies | Absent in 10 g |

TABLE 4

Probiotic-Lager BEER stability studies at 40 ± 2° C., 65% ± 5% Relative humidity.

| S. No. | Tests performed | Initial | 1 | 2 | 3 | 6 | Limit |
|---|---|---|---|---|---|---|---|
| | | Period of Testing (month) | | | | | |
| 1. | Description | Complies | Complies | Complies | Complies | Complies | Pale brown liquid |
| 2. | Specific gravity | 1.0072 | 1.0073 | 1.0074 | 1.0071 | 1.0075 | Record |
| 3. | pH | 3.93 | 3.91 | 3.89 | 3.88 | 3.86 | Record |
| 4. | Alcohol content by GC | 3.48% | 3.42% | 3.41% | 3.49% | 3.44% | Record |
| 5. | Other Aerobic micro-organism count | <100 cfu/ml | <100 cfu/ml | <100 cfu/ml | <100 cfu/ml | <100 cfu/ml | <100 cfu/ml |
| 6. | Yeasts and molds count | Complies | Complies | Complies | Compiles | Complies | NMT100 cfu/g |
| 7. | Enterobacteriacea | Complies | Compiles | Compiles | Compiles | Complies | NMT100 cfu/g |
| 8. | Conforms | Complies | Complies | Complies | Complies | Complies | NMT10 cfu/g |
| 9. | Pathogens (*Escherichia coli*, *Staphylococcus aureus*, *Pseudomonas aeruginosa*, *Salmonella* spp.) | Complies | Complies | Complies | Complies | Complies | Absent in 10 g |

TABLE 5

Probiotic-Strong Lager BEER stability studies at 40 ± 2° C., 65% ± 5% Relative humidity.

| S. No. | Tests performed | Initial | 1 | 2 | 3 | 6 | Limit |
|---|---|---|---|---|---|---|---|
| 1. | Description | Complies | Complies | Complies | Complies | Complies | Pale brown liquid |
| 2. | Specific gravity | 1.0071 | 1.0069 | 1.0072 | 1.0073 | 1.0074 | Record |
| 3. | pH | 3.91 | 3.89 | 3.88 | 3.86 | 3.85 | Record |
| 4. | Alcohol content by GC | 4.81% | 4.85% | 4.89% | 4.82% | 4.79% | Record |
| 5. | Other Aerobic micro-organism count | <100 cfu/ml | <100 cfu/ml | <100 cfu/ml | <100 cfu/ml | <100 cfu/ml | Record |
| 6. | Yeasts and molds count | Complies | Complies | Complies | Complies | Complies | NMT100 cfu/g |
| 7. | Enterobacteriaceae | Complies | Complies | Complies | Complies | Complies | NMT100 cfu/g |
| 8. | Coliforms | Complies | Complies | Complies | Complies | Complies | NMT10 cfu/g |
| 9. | Pathogens (*Escherichia coli*, *Staphylococcus aureus*, *Pseudomonas aeruginosa*, *Salmonella* spp.) | Complies | Complies | Complies | Complies | Complies | Absent in 10 g |

TABLE 6

Probiotic-Whisky stability studies at 40 ± 2° C., 65% ± 5% Relative humidity.

| S. No. | Tests performed | Initial | 1 | 2 | 3 | 6 | Limit |
|---|---|---|---|---|---|---|---|
| 1. | Description | Complies | Complies | Complies | Complies | Complies | Pale brown liquid |
| 2. | Specific gravity | 0.9452 | 0.9425 | 0.9450 | 0.9451 | 0.9451 | Record |
| 3. | pH | 6.21 | 5.79 | 5.62 | 5.51 | | Record |
| 4. | Alcohol content by GC | 42.8% | 42.88% | 42.58% | 42.17% | 42.67% | Record |
| 5. | Other Aerobic micro-organism count | <100 cfu/ml | <100 cfu/ml | <100 cfu/ml | <100 cfu/ml | <100 cfu/ml | Record |
| 6. | Yeasts and molds count | Complies | Complies | Complies | Complies | Complies | NMT100 cfu/g |
| 7. | Enterobacteriaceae | Complies | Complies | Complies | Complies | Complies | NMT100 cfu/g |
| 8. | Coliforms | Complies | Complies | Complies | Complies | Complies | NMT10 cfu/g |
| 9. | Pathogens (*Escherichia coli*, *Staphylococcus aureus*, *Pseudomonas aeruginosa*, *Salmonella* spp,) | Complies | Complies | Complies | Complies | Complies | Absent in 10 g |

TABLE 7

Probiotic-Mild Lager BEER stability studies at 25 ± 2° C., 60% ± 5% Relative humidity.

| S. No. | Tests performed | Initial | 3 | 6 | Limit |
|---|---|---|---|---|---|
| 1. | Description | Complies | Complies | Complies | Pale brown liquid |
| 2. | Specific gravity | 1.0081 | 1.0083 | 1.0086 | Record |
| 3. | pH | 3.86 | 3.85 | 3.74 | Record |
| 4. | Alcohol content by GC | 3.34% | 3.37% | 3.38% | Record |
| 5. | Other Aerobic micro-organism count | <100 cfu/ml | <100 cfu/ml | <100 cfu/ml | Record |
| 6. | Yeasts and molds count | Complies | Complies | Complies | NMT100 cfu/g |
| 7. | *Enterobacteriaceae* | Complies | Complies | Complies | NMT100 cfu/g |
| 8. | Coliforms | Complies | Complies | Complies | NMT10 cfu/g |
| 9. | Pathogens (*Escherichia coli, Staphylococcus aureus, Pseudomonas aeruginosa, Salmonella* spp.) | Complies | Complies | Complies | Absent in 10 g |

TABLE 8

Probiotic-Lager BEER stability studies at 25 ± 2° C., 60% ± 5% Relative humidity.

| S. No. | Tests performed | Initial | 1 | 6 | Limit |
|---|---|---|---|---|---|
| 1. | Description | Complies | Complies | Complies | Pale brown liquid |
| 2. | Specific gravity | 1.0073 | 1.0071 | 1.0074 | Record |
| 3. | pH | 3.93 | 3.95 | 3.82 | Record |
| 4 | Alcohol content by GC | 3.48% | 3.45% | 3.47% | Record |
| 5. | Other Aerobic micro-organism count | <100 cfu/ml | <100 cfu/ml | <100 cfu/ml | Record |
| 6. | Yeasts and molds count | Complies | Complies | Complies | NMT100 cfu/g |
| 7. | *Enterobacteriaceae* | Complies | Complies | Complies | NMT100 cfu/g |
| 8. | Coliforms | Complies | Complies | Complies | NMT10 cfu/g |
| 9. | Pathogens (*Escherichia coli, Staphylococcus aureus, Pseudomonas aeruginosa, Salmonella* spp.) | Complies | Complies | Complies | Absent in 10 g |

TABLE 9

Probiotic-Strong Lager BEER stability studies at 25 ± 2° C., 60% ± 5% Relative humidity.

| S. No. | Tests performed | Initial | 3 | 6 | Limit |
|---|---|---|---|---|---|
| 1. | Description | Complies | Complies | Complies | Pale brown liquid |
| 2. | Specific gravity | 1.0075 | 1.0064 | 1.0077 | Record |
| 3. | pH | 3.91 | 3.85 | 3.81 | Record |
| 4. | Alcohol content by GC | 4.81% | 4.87% | 4.75% | Record |
| 5. | Other Aerobic micro-organism count | <100 cfu/ml | <100 cfu/ml | <100 cfu/ml | Record |
| 6. | Yeasts and molds count | Complies | Complies | Complies | NMT100 cfu/g |
| 7. | *Enterobacteriaceae* | Complies | Complies | Complies | NMT100 cfu/g |
| 8. | Coliforms | Complies | Complies | Complies | NMT10 cfu/g |
| 9. | Pathogens (*Escherichia coli, Staphylococcus aureus, Pseudomonas aeruginosa, Salmonella* spp.) | Complies | Complies | Complies | Absent in 10 g |

TABLE 10

Probiotic-Whisky (Batch: FT/WHL/02) stability studies at 25 ± 2° C., 60% ± 5% Relative humidity.

| S. No. | Tests performed | Initial | 3 | 6 | Limit |
|---|---|---|---|---|---|
| 1. | Description | Complies | Complies | Complies | Pale brown liquid |
| 2. | Specific gravity | 0.9453 | 0.9455 | 0.9457 | Record |
| 3. | pH | 6.21 | 5.57 | 5.48 | Record |
| 4. | Alcohol content by GC | 42.8% | 42.27% | 42.84% | Record |
| 5. | Other Aerobic micro-organism count | <100 cfu/ml | <100 cfu/ml | <100 cfu/ml | Record |
| 6. | Yeasts and molds count | Complies | Complies | Complies | NMT100 cfu/ml |
| 7. | *Enterobacteriaceae* | Complies | Complies | Complies | NMT100 cfu/ml |
| 8. | Coliforms | Complies | Complies | Complies | NMT10 cfu/ml |
| 9. | Pathogens (*Escherichia coli, Staphylococcus aureus, Pseudomonas aeruginosa, Salmonella* spp.) | Complies | Complies | Complies | Absent in 10 g |

Results of the stability studies of alcoholic beverages (beer and whisky) suggested that inclusion of probiotic strain *B. coagulans* MTCC 5856 did not affect the Specific gravity, pH and Alcohol content suggesting its compatibility and stability when stored at room temperature (25±2° C., 60%±5% Relative humidity) and accelerated conditions (40±2° C., 65%±5% Relative humidity).

Further, there was no significant change in the microbial parameter was observed suggesting that probiotic alcoholic beverage did not alter the microbial profile.

Example 2: Methods of Brewing Alcoholic Beverage with Probiotic

The different methods for brewing alcoholic beverage by adding probiotic bacterial *Bacillus coagulans* is disclosed herewith.

Method 1: Addition of *Bacillus coagulans* in Pre-Fermentation Stage

Figure 1B:
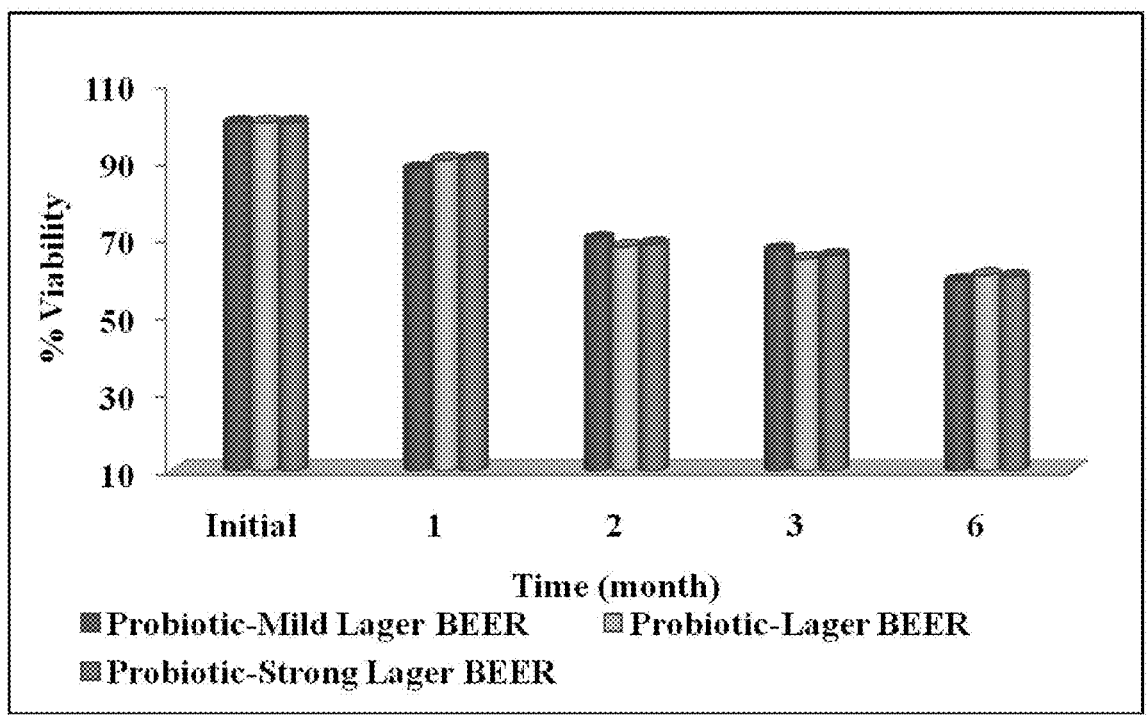
FIG. 1*b* is the graphical representation showing percentage viability of probiotic bacteria *Bacillus coagulans* in alcoholic beverage, added during the step of malting while brewing the beverage.
Figure 9:
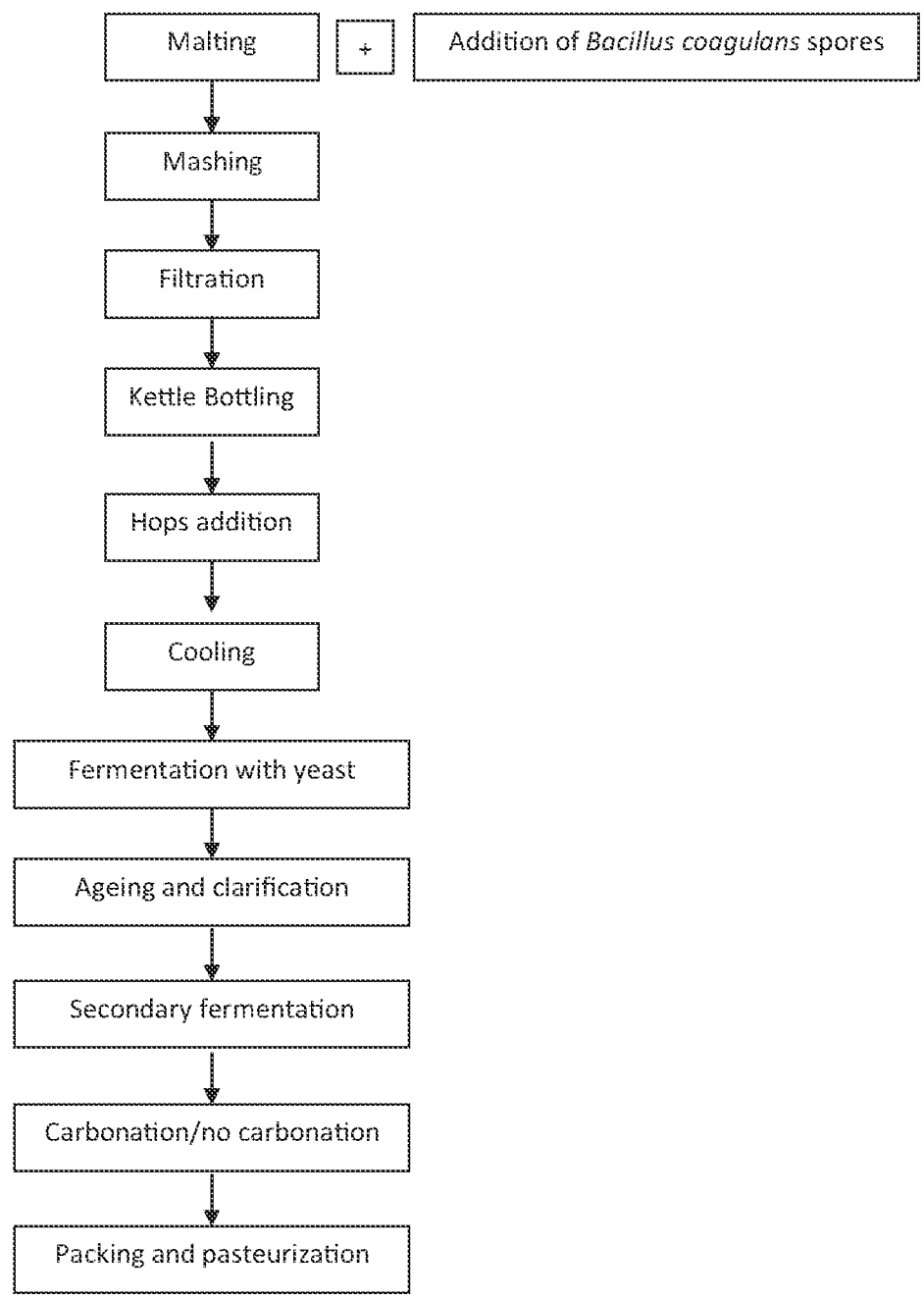
FIG. 9 is a flow chart describing the method of brewing alcoholic beverage by the addition of *Bacillus coagulans* at the stage of malting.

The flow chart in FIG. 9 describes the method of brewing alcoholic beverage by the addition of *Bacillus coagulans* at the stage of malting The stability and viability of *Bacillus coagulans* spore/vegetative cells were tested. The results indicated that *Bacillus coagulans* showed increased stability (FIG. 1*a*) and viability (FIG. 1*b*) when added at the stage of malting.

Figure 2A:
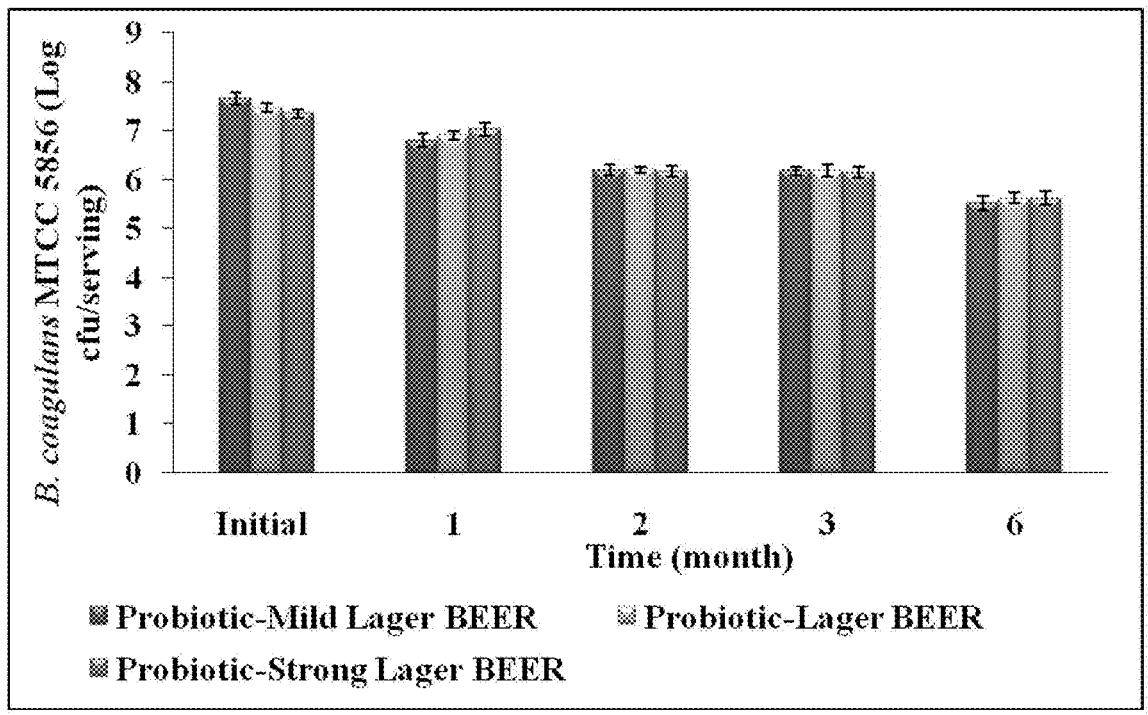
FIG. 2*a* is the graphical representation showing the stability of probiotic bacteria *Bacillus coagulans* in alcoholic beverage, added during the step of Hops addition while brewing the beverage.
Figure 2B:
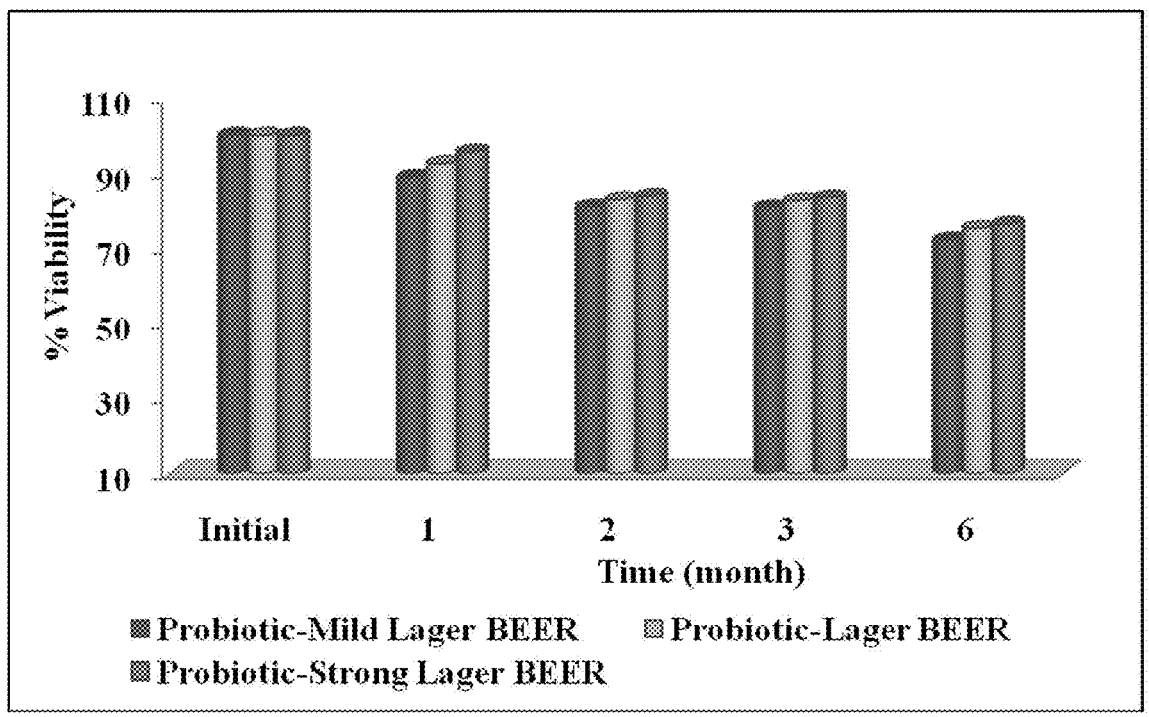
FIG. 2*b* is the graphical representation showing percentage viability of probiotic bacteria *Bacillus coagulans* in alcoholic beverage, added during the step of Hops addition while brewing the beverage.
Figure 3A:
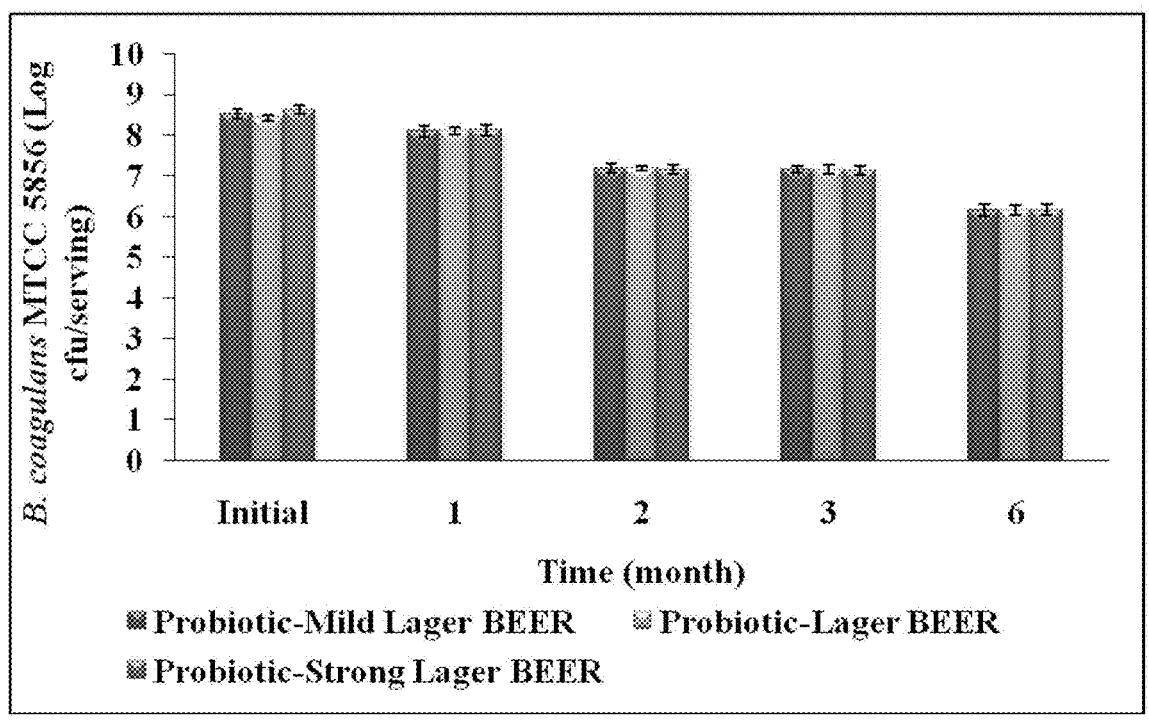
FIG. 3*a* is the graphical representation showing the stability of probiotic bacteria *Bacillus coagulans* in alcoholic beverage, added during the step of fermentation while brewing the beverage.
Figure 3B:
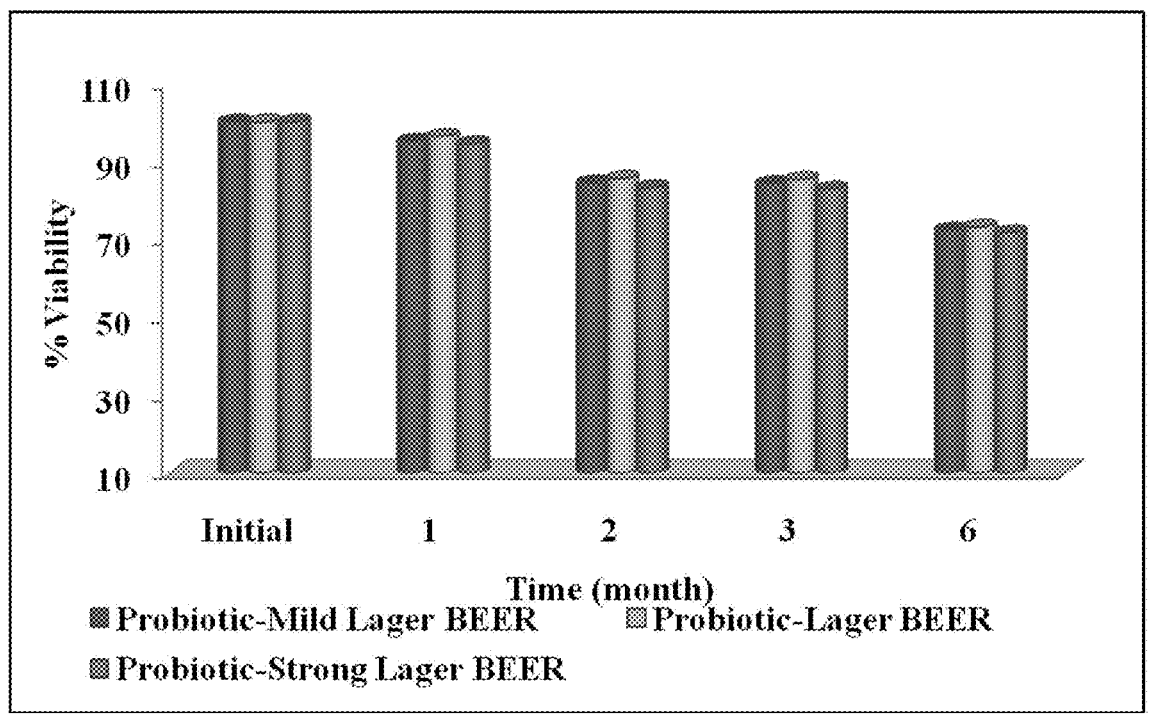
FIG. 3*b* is the graphical representation showing percentage viability of probiotic bacteria *Bacillus coagulans* in alcoholic beverage, added during the step of fermentation while brewing the beverage.
Figure 10:
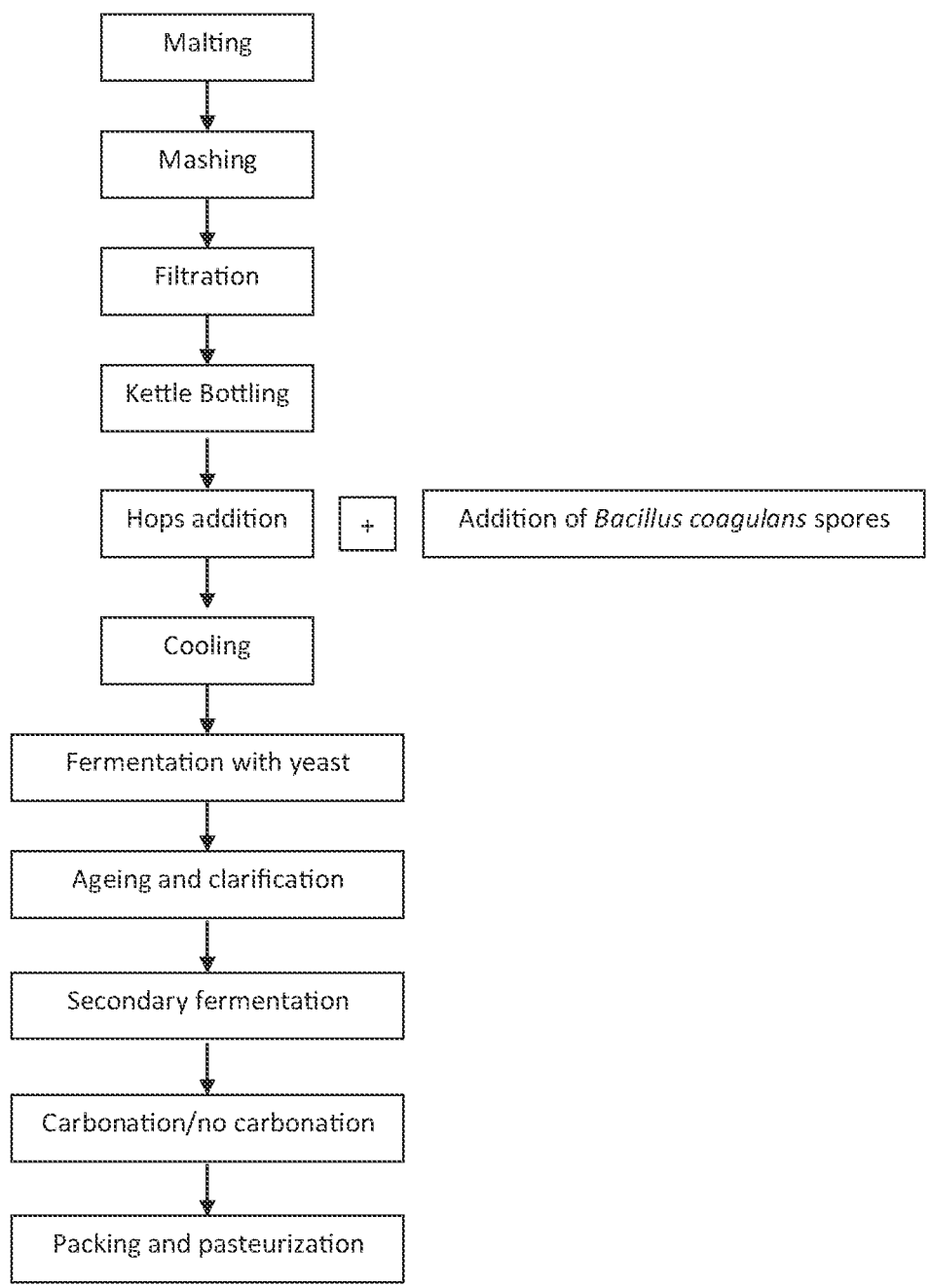
FIG. 10 is a flow chart describing the method of brewing alcoholic beverage by the addition of *Bacillus coagulans* at the stage of hops addition.
Figure 11:
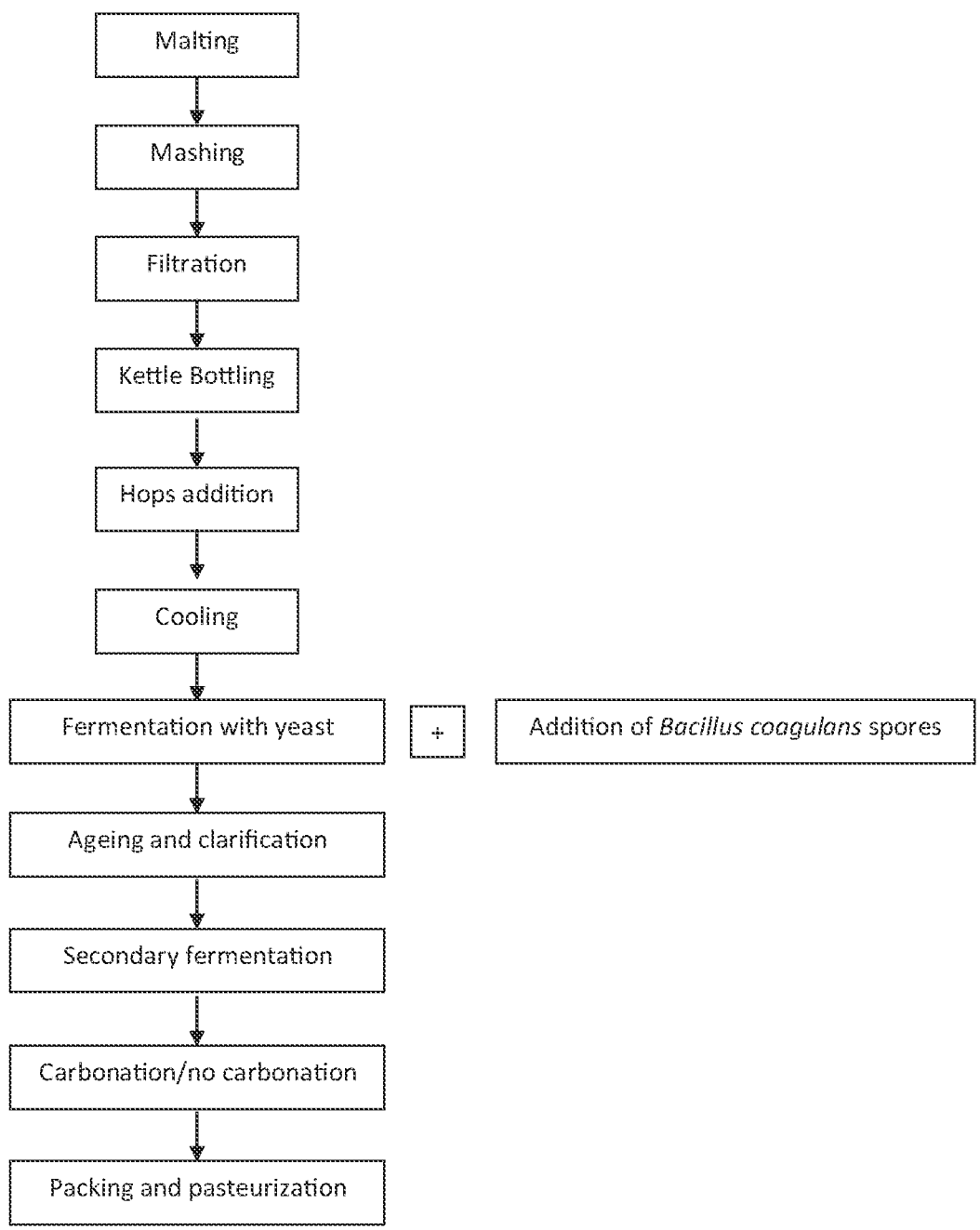
FIG. 11 is a flow chart describing the method of brewing alcoholic beverage by the addition of *Bacillus coagulans* during the fermentation stage.

Method 2: Addition of *Bacillus coagulans* in Pre-Fermentation Stage at the Stage of Hops Addition The flow chart in FIG. 10 describes the method of brewing alcoholic beverage by the addition of *Bacillus coagulans* at the stage of hops addition The stability and viability of *Bacillus coagulans* spore/vegetative cells were tested. The results indicated that *Bacillus coagulans* showed increased stability (FIG. 2*a*) and viability (FIG. 2*b*) when added at the stage of Hops addition Method 3: Addition of *Bacillus coagulans* During Fermentation The flow chart in FIG. 1 describes the method of brewing alcoholic beverage by the addition of *Bacillus coagulans* during the fermentation stage The stability and viability of *Bacillus coagulans* spore/vegetative cells were tested. The results indicated that *Bacillus coagulans* showed increased stability (FIG. 3*a*) and viability (FIG. 3*b*) when added during the fermentation stage.

Method 4: Addition of *Bacillus coagulans* During Secondary Fermentation

Figure 4A:
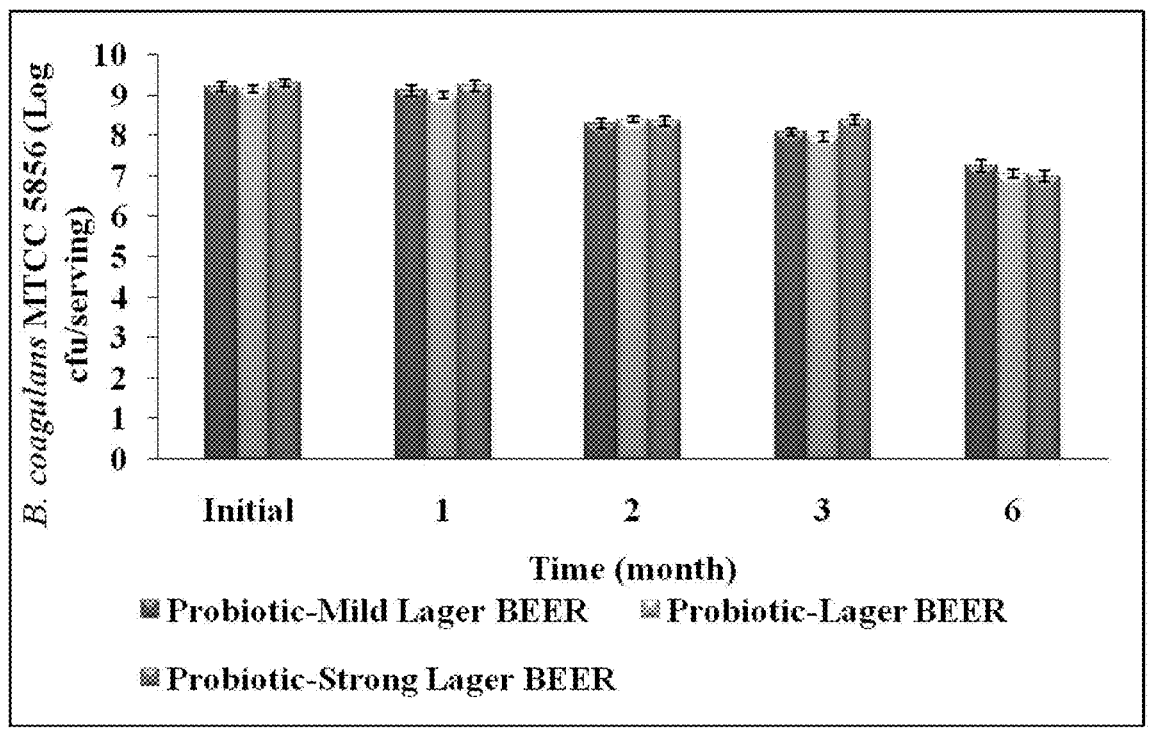
FIG. 4*a* is the graphical representation showing the stability of probiotic bacteria *Bacillus coagulans* in alcoholic beverage, added during the step of secondary fermentation while brewing the beverage.
Figure 4B:
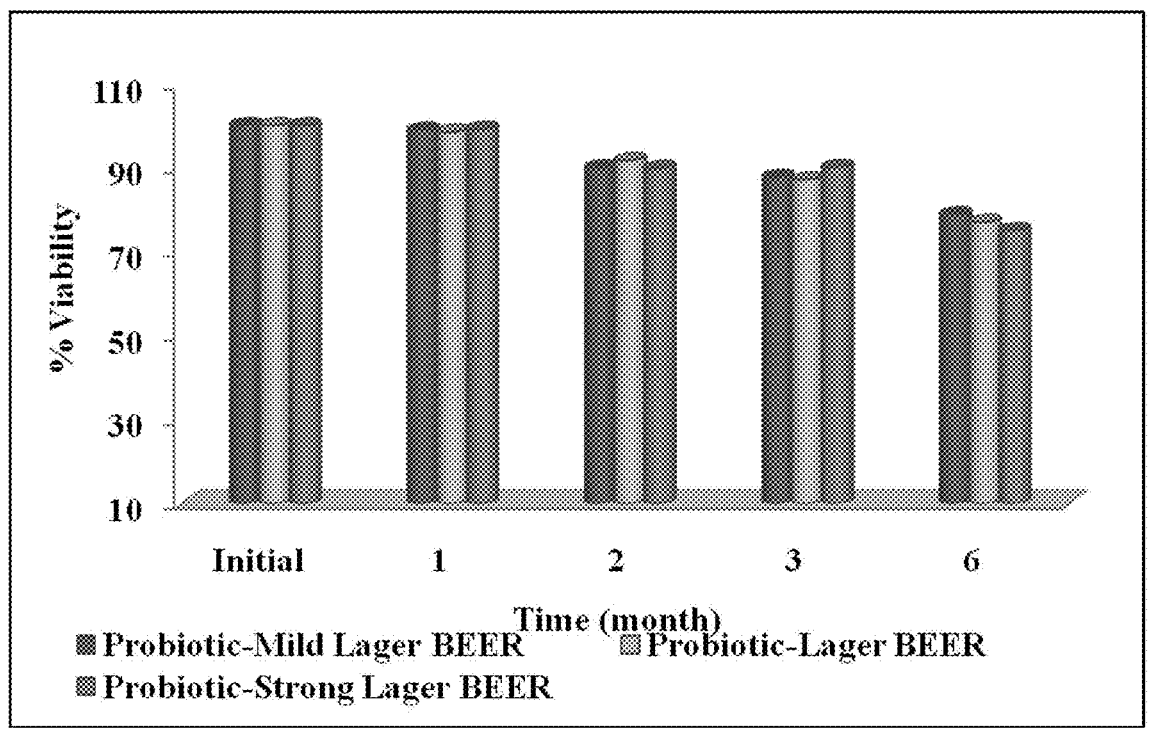
FIG. 4*b* is the graphical representation showing percentage viability of probiotic bacteria *Bacillus coagulans* in alcoholic beverage, added during the step of secondary fermentation while brewing the beverage.
Figure 12:
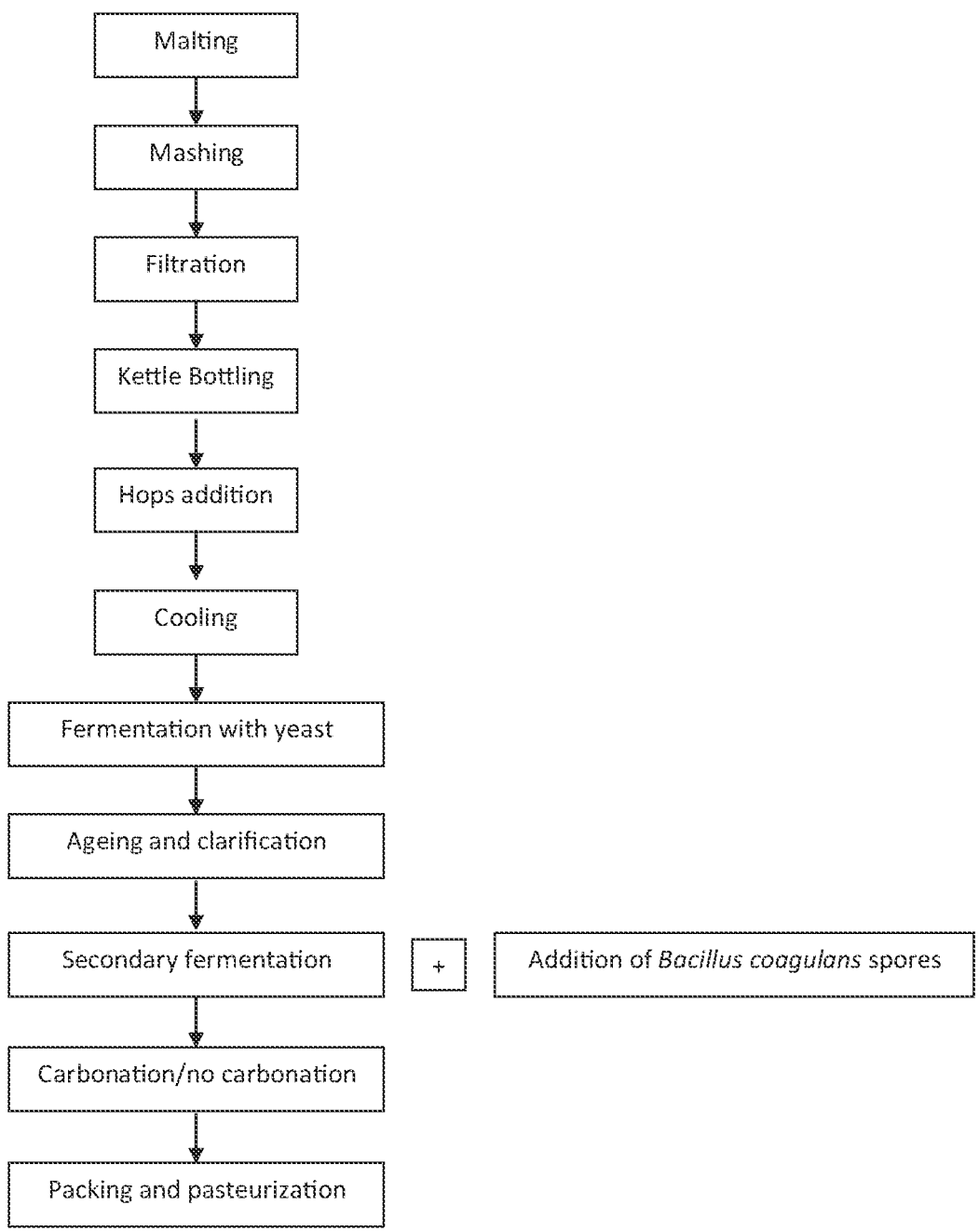
FIG. 12 is a flow chart describing the method of brewing alcoholic beverage by the addition of *Bacillus coagulans* during the secondary fermentation stage.

The flow chart in FIG. 12 describes the method of brewing alcoholic beverage by the addition of *Bacillus coagulans* during the secondary fermentation stage The stability and viability of *Bacillus coagulans* spore/vegetative cells were tested. The results indicated that *Bacillus coagulans* showed increased stability (FIG. 4*a*) and viability (FIG. 4*b*) when added during the secondary fermentation stage.

Figure 5A:
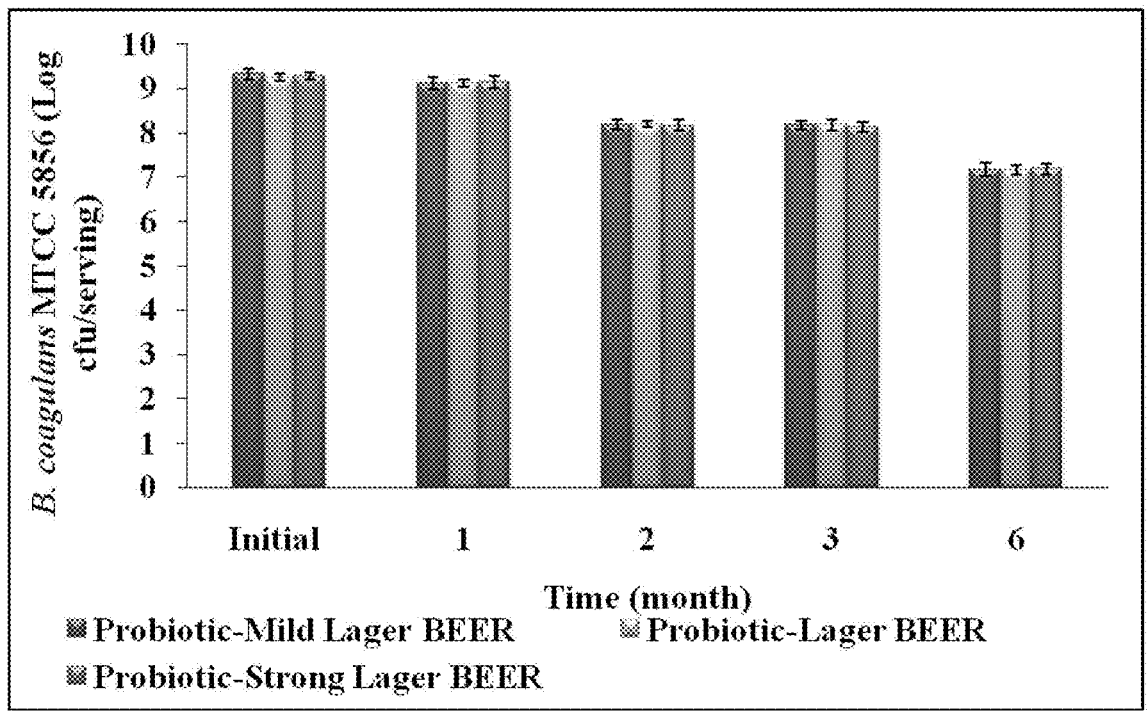
FIG. 5a is the graphical representation showing the stability of probiotic bacteria *Bacillus coagulans* in alcoholic beverage, added during the step of carbonation while brewing the beverage.
Figure 5B:
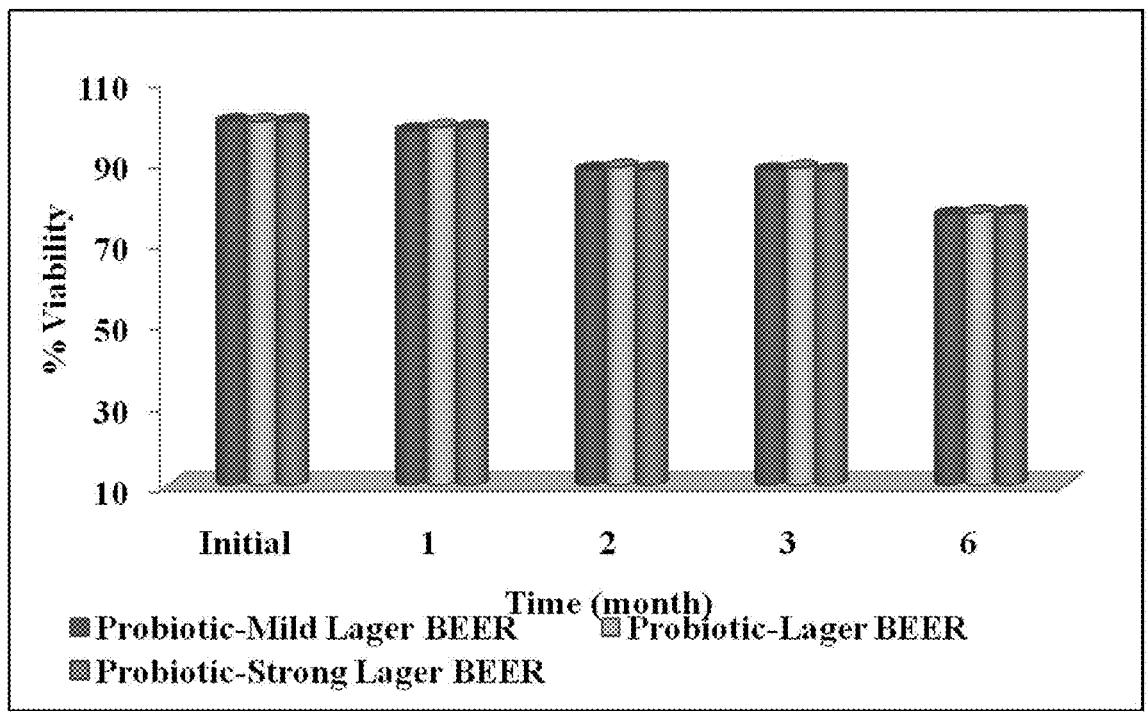
FIG. 5b is the graphical representation showing percentage viability of probiotic bacteria *Bacillus coagulans* in alcoholic beverage, added during the step of carbonation while brewing the beverage.
Figure 13:
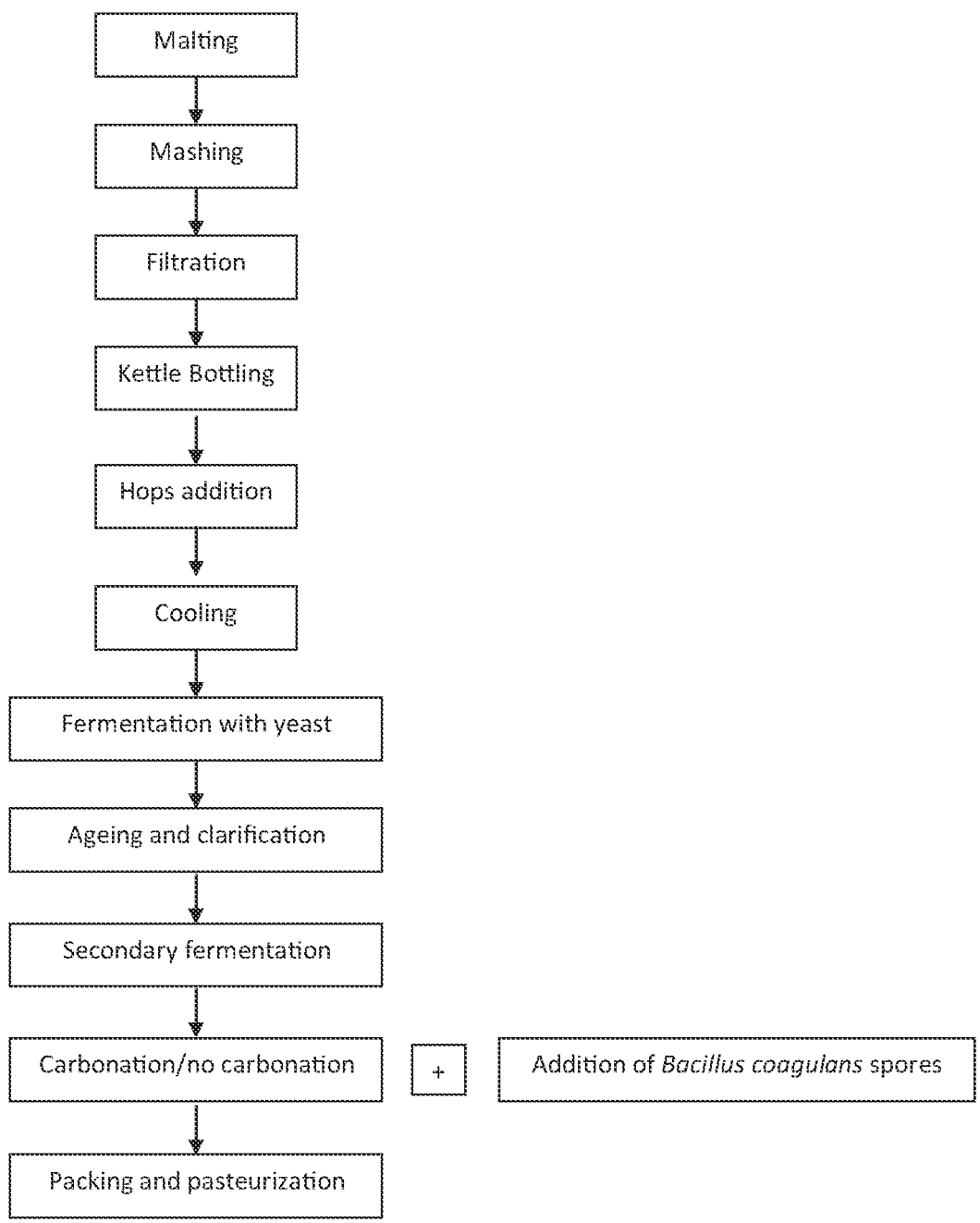
FIG. 13 is a flow chart describing the method of brewing alcoholic beverage by the addition of *Bacillus coagulans* at the step of carbonation.

Method 5: Addition of *Bacillus coagulans* During Post Fermentation Stage at the Step of Carbonation The flow chart in FIG. 13 describes the method of brewing alcoholic beverage by the addition of *Bacillus coagulans* at the step of carbonation The stability and viability of *Bacillus coagulans* spore/vegetative cells were tested. The results indicated that *Bacillus coagulans* showed increased stability (FIG. 5*a*) and viability (FIG. 5*b*) when added during the post fermentation stage of carbonation.

Figure 6A:
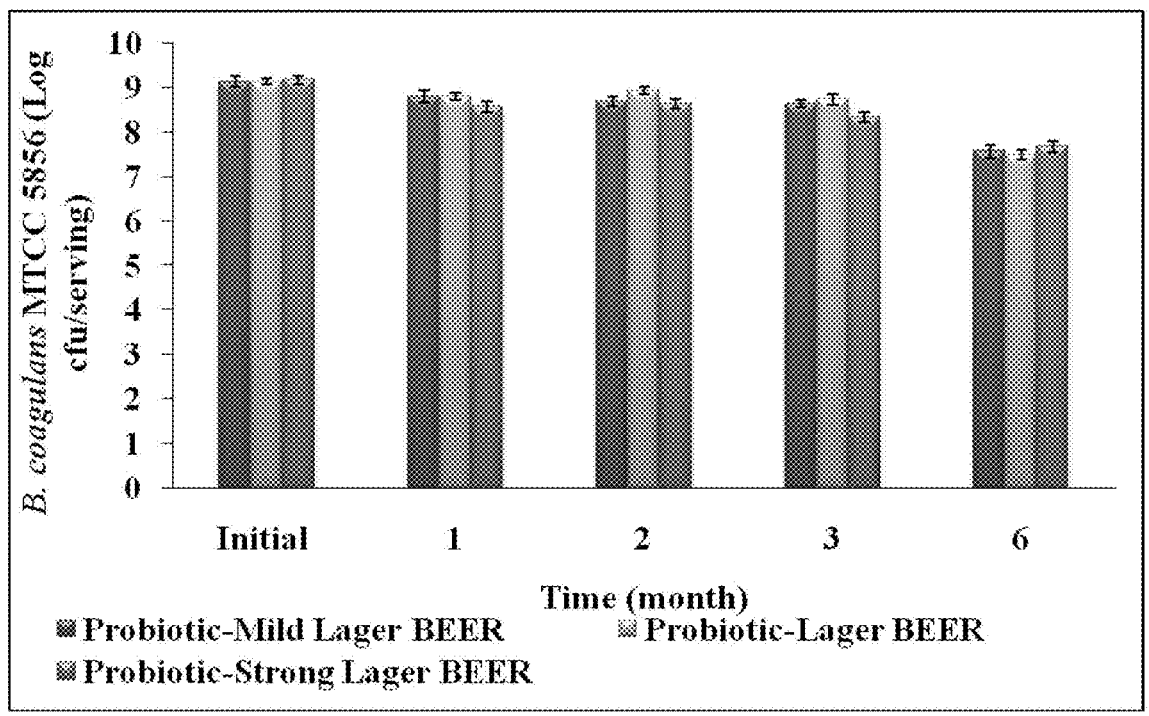
FIG. 6a is the graphical representation showing the stability of probiotic bacteria *Bacillus coagulans* in alcoholic beverage, added during the step of packing and pasteurization while brewing the beverage.
Figure 6B:
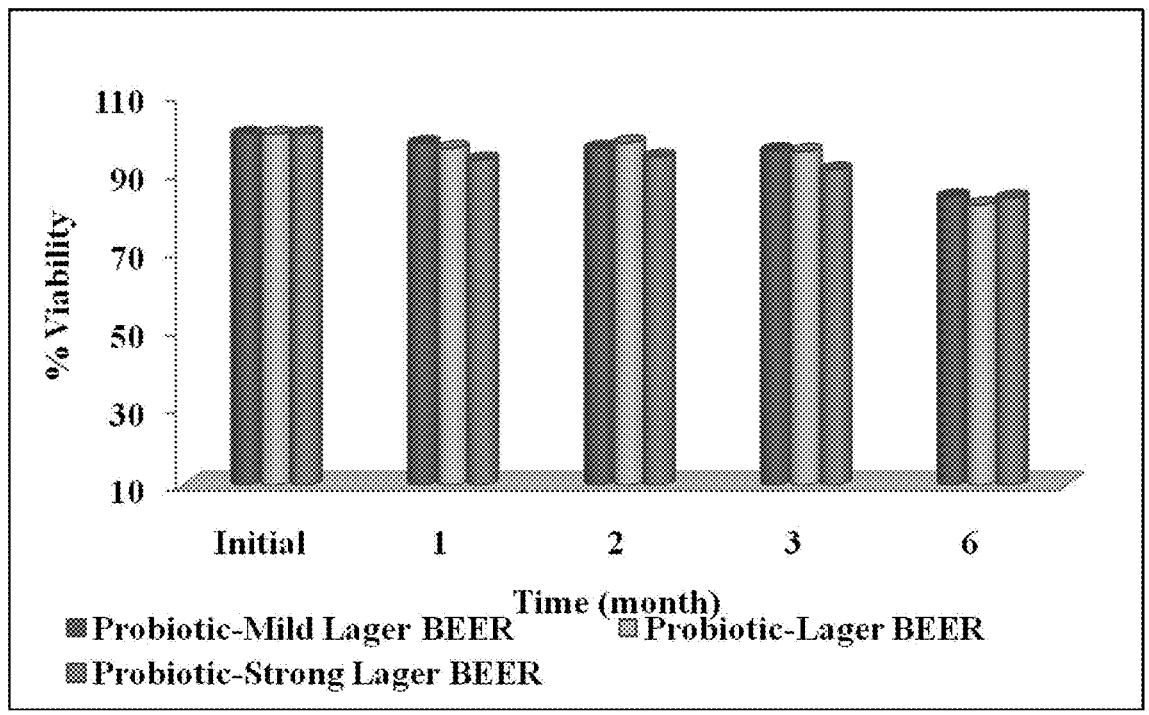
FIG. 6b is the graphical representation showing percentage viability of probiotic bacteria *Bacillus coagulans* in alcoholic beverage, added during the step of packing and pasteurization while brewing the beverage.
Figure 14:
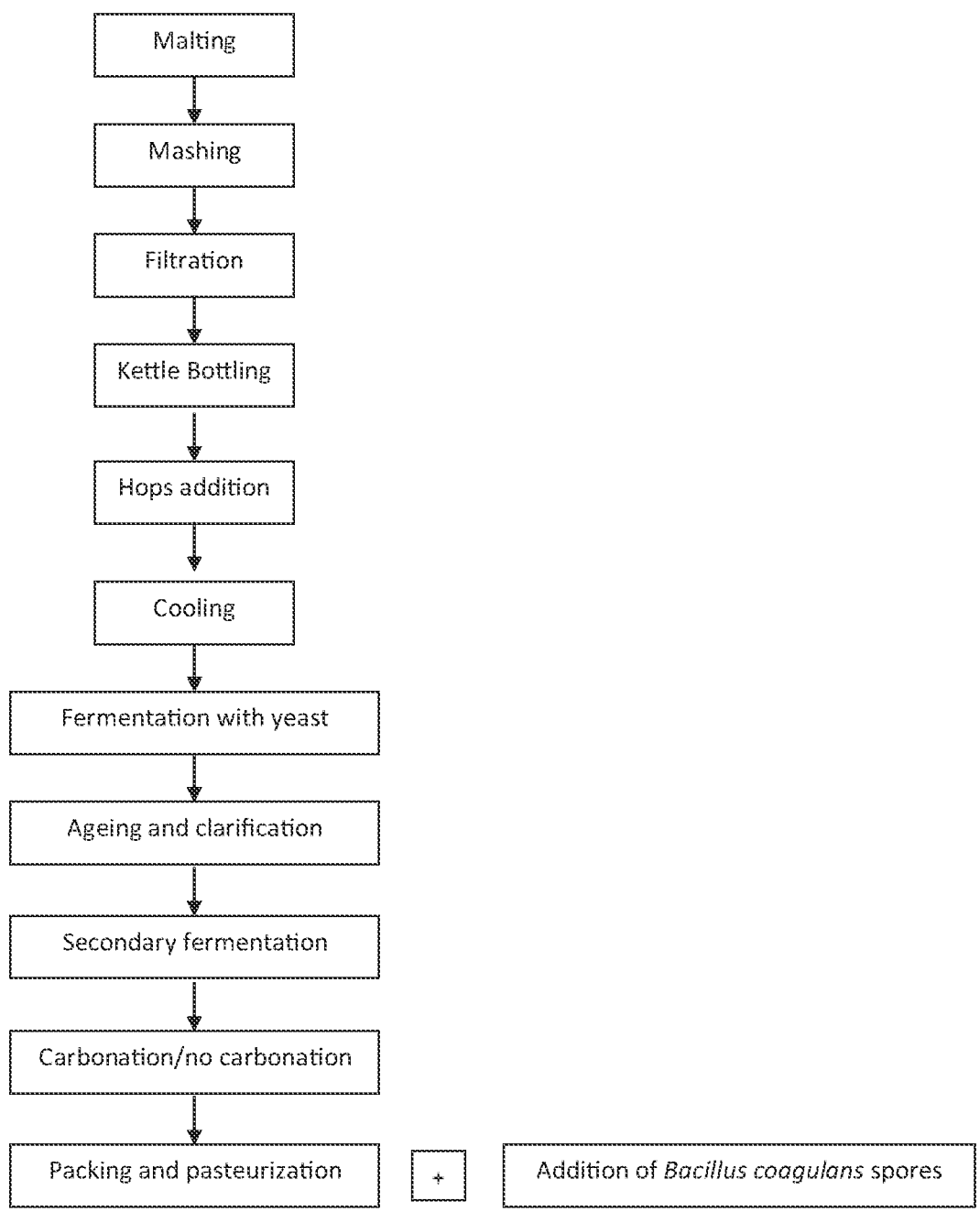
FIG. 14 is a flow chart describing the method of brewing alcoholic beverage by the addition of *Bacillus coagulans* at the step of packing and pasteurization.

Method 6: Addition of *Bacillus coagulans* During Post Fermentation Stage at the Step of Packing and Pasteurization The flow chart in FIG. 14 describes the method of brewing alcoholic beverage by the addition of *Bacillus coagulans* at the step of packing and pasteurization The stability and viability of *Bacillus coagulans* spore/vegetative cells were tested. The results indicated that *Bacillus coagulans* showed increased stability (FIG. 6*a*) and viability (FIG. 6*b*) when added during the post fermentation stage of packing and pasteurization.

Method 7: Addition of *Bacillus coagulans* During Post Fermentation Stage

Figure 7A:
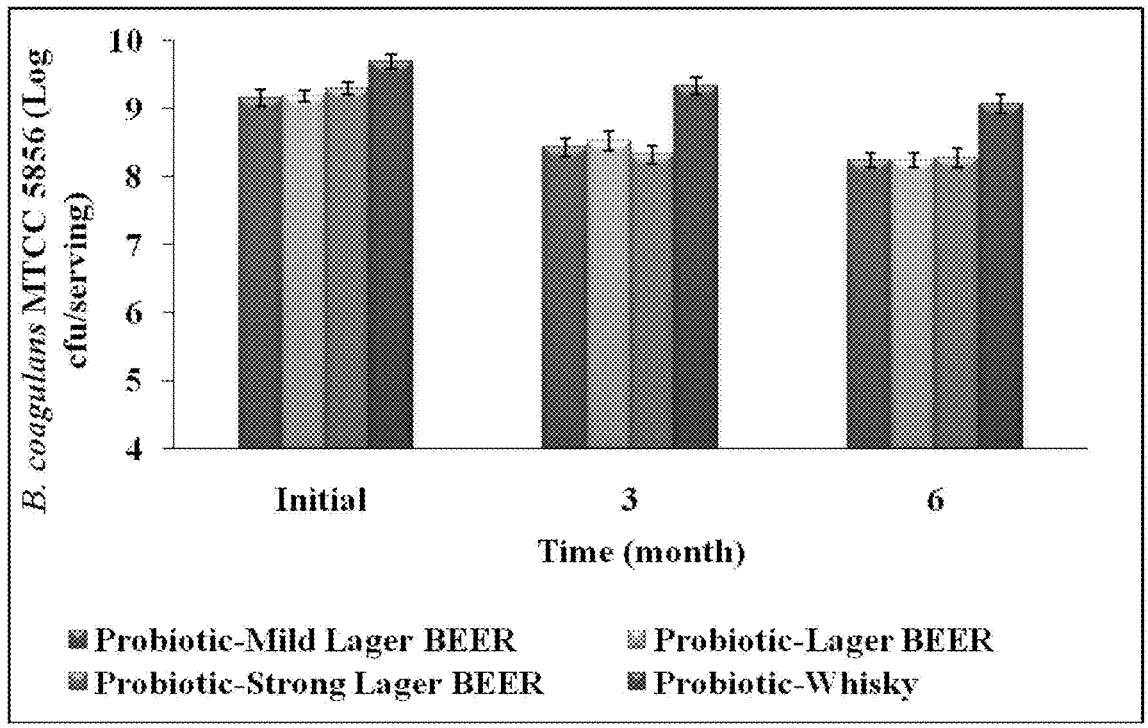
FIG. 7a is the graphical representation showing the stability of probiotic bacteria *Bacillus coagulans* in alcoholic beverage at 25° C., added during the step of packing and pasteurization followed by carbonation while brewing the beverage.
Figure 7B:
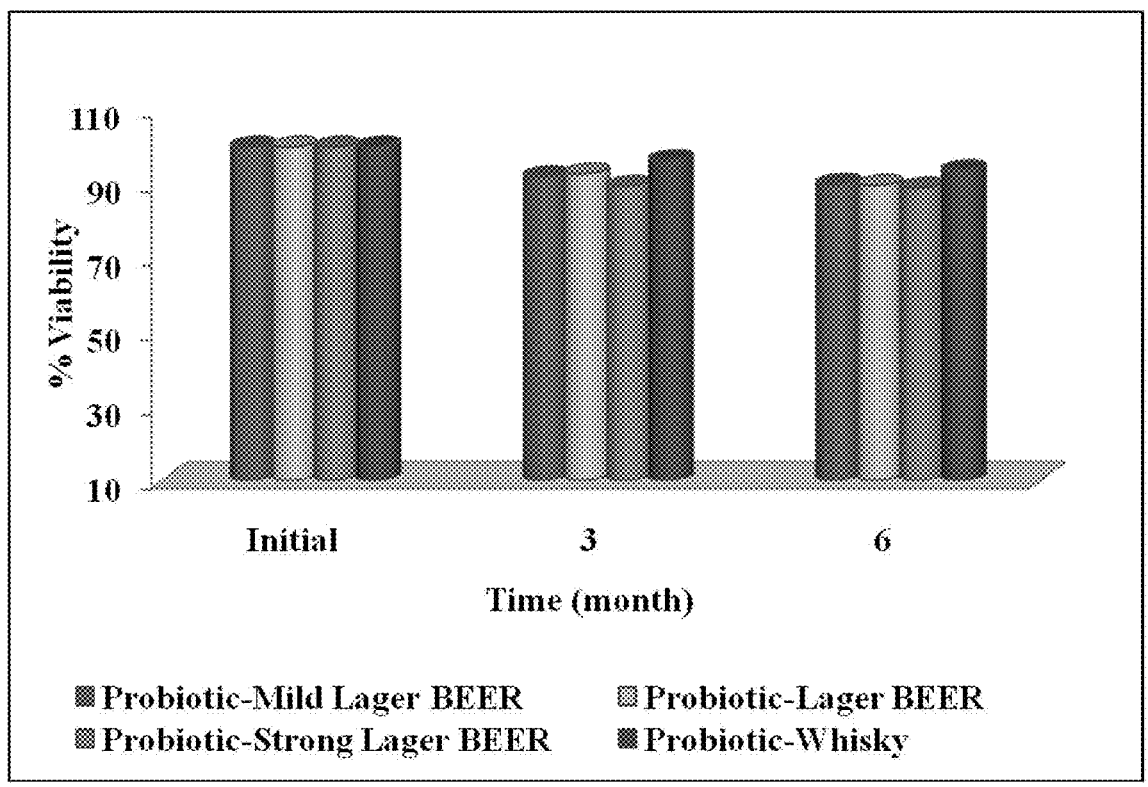
FIG. 7b is the graphical representation showing percentage viability of probiotic bacteria *Bacillus coagulans* in alcoholic beverage at 25° C., added during the step of packing and pasteurization followed by carbonation while brewing the beverage.
Figure 8A:
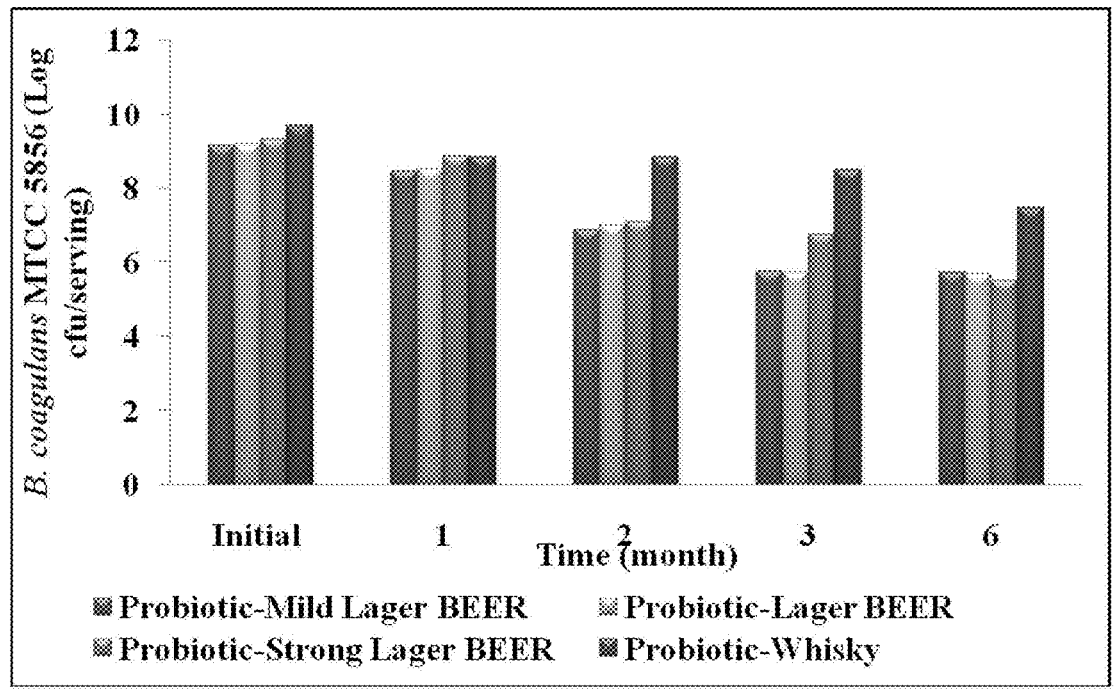
FIG. 8b is the graphical representation showing percentage viability of probiotic bacteria *Bacillus coagulans* in alcoholic beverage at 40° C., added during the step of packing and pasteurization followed by carbonation while brewing the beverage.
Figure 8B:
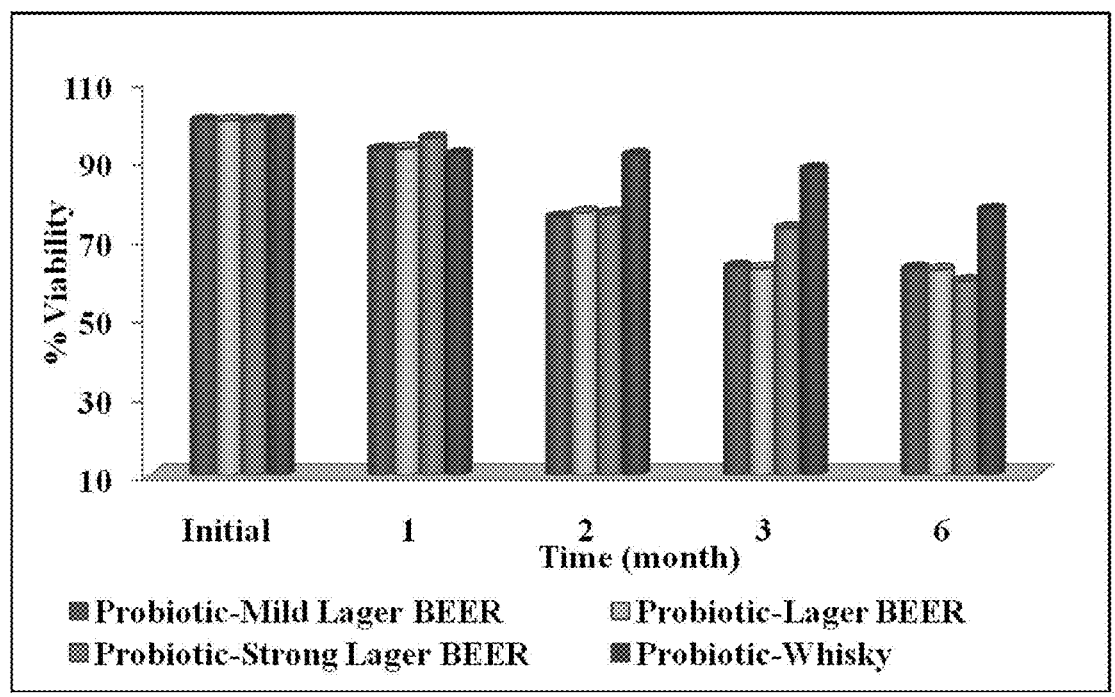
Figure 15:
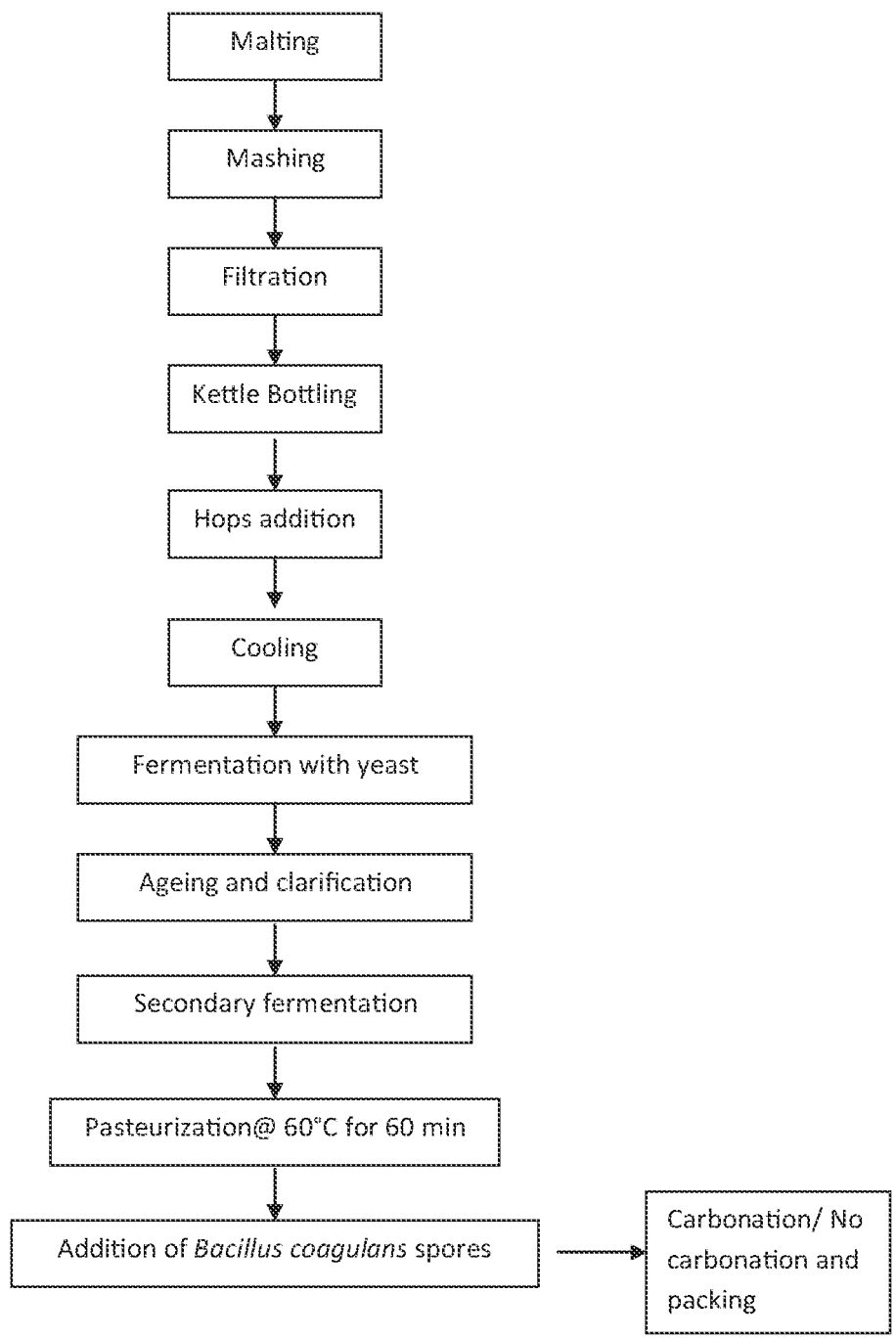
FIG. 15 is a flow chart describing the method of brewing alcoholic beverage by the addition of *Bacillus coagulans* at the step of packing and pasteurization.

The flow chart in FIG. 15 describes the method of brewing alcoholic beverage by the addition of *Bacillus coagulans* at the step of packing and pasteurization The stability and viability of *Bacillus coagulans* spore/vegetative cells were tested. The results indicated that *Bacillus coagulans* showed increased stability at 25° C. (FIG. 7*a*) and 40° C. (FIG. 8*a*) and viability at 25° C. (FIG. 7*b*) and 40° C. (FIG. 8*b*) when added during the post fermentation stage.

The above results indicate that the *Bacillus coagulans* is stable and viable during the entire fermentation process and is the first go-to-probiotic to be added along with alcoholic beverages.

The deposit of biological material *Bacillus coagulans* SBC37-01 bearing accession number MTCC 5856, mentioned in the instant application has been made on 19 Sep. 2013 at Microbial Type Culture Collection & Gene Bank (MTCC), CSTR-Institute of Microbial Technology, Sector 39-A, Chandigarh—160036, India.

While the invention has been described with reference to a preferred embodiment, it is to be clearly understood by those skilled in the art that the invention is not limited thereto. Rather, the scope of the invention is to be interpreted only in conjunction with the appended claims.

We claim:

1. An alcoholic beverage composition comprising probiotic bacteria *Bacillus coagulans* MTCC 5856 in the form of spores wherein said spores exhibit high recovery, tolerability, compatibility and viability after brewing.

2. The alcoholic beverage composition comprising *Bacillus coagulans* MTCC 5856 as in claim 1, wherein the alcoholic beverage is selected from the group consisting of Beer, and whisky.

3. The composition of claim 1, wherein the alcohol content is between 1% to 43%.

4. The composition of claim 1, wherein the *Bacillus coagulans* live spores are present in the alcoholic beverages at a concentration of $1 \times 10^6$ to $1 \times 10^{12}$.

* * * * *